(12) United States Patent
Fornoff

(10) Patent No.: US 8,636,505 B2
(45) Date of Patent: Jan. 28, 2014

(54) CARRIER FOR A FASTENING ELEMENT TO BE FABRICATED AND A METHOD FOR PRODUCTION THEREOF, PARTICULARLY AS AN ORTHODONTIC BRACKET

(75) Inventor: Peter Fornoff, Relchelsheim (DE)

(73) Assignee: Sirona Dental Systems GmbH, Bensheim (DE)

( * ) Notice: Subject to any disclaimer, the term of this patent is extended or adjusted under 35 U.S.C. 154(b) by 27 days.

(21) Appl. No.: 11/436,051

(22) Filed: May 18, 2006

(65) Prior Publication Data

US 2006/0275729 A1     Dec. 7, 2006

Related U.S. Application Data

(60) Provisional application No. 60/755,085, filed on Jan. 3, 2006.

(30) Foreign Application Priority Data

Jun. 1, 2005 (DE) .......................... 10 2005 025 557

(51) Int. Cl.
*A61C 3/00* (2006.01)
*A61C 1/14* (2006.01)
*B21F 43/00* (2006.01)

(52) U.S. Cl.
USPC ................................ 433/3; 433/49; 29/896.11

(58) Field of Classification Search
USPC ............... 433/2, 3, 49, 50, 77, 79, 163, 8–16; 29/896.11; 206/63.5; 264/16–18; 408/44–45; 269/287–288, 71, 73, 46, 269/47, 126
See application file for complete search history.

(56) References Cited

U.S. PATENT DOCUMENTS

| | | | |
|---|---|---|---|
| 4,284,405 A | | 8/1981 | Dellinger |
| 4,901,847 A | * | 2/1990 | Kesling ........................ 206/63.5 |
| 4,921,378 A | * | 5/1990 | Kytola .......................... 409/221 |
| 5,212,857 A | * | 5/1993 | McMurtry ..................... 29/38 C |
| 5,522,725 A | * | 6/1996 | Jordan et al. ...................... 433/9 |
| 5,827,058 A | | 10/1998 | Kelly et al. ....................... 433/9 |
| 5,931,667 A | * | 8/1999 | Papandreas ....................... 433/8 |
| 6,015,289 A | | 1/2000 | Andreiko et al. .................. 433/3 |
| 6,089,861 A | * | 7/2000 | Kelly et al. ....................... 433/9 |
| 6,185,802 B1 | * | 2/2001 | Gruber et al. ................. 29/38 R |
| 2003/0194677 A1 | | 10/2003 | Sachdeva et al. |
| 2004/0115586 A1 | | 6/2004 | Andreiko et al. |
| 2004/0219471 A1 | | 11/2004 | Cleary et al. ...................... 433/3 |
| 2004/0219473 A1 | | 11/2004 | Cleary et al. |
| 2005/0008989 A1 | * | 1/2005 | Rothenberger et al. .... 433/202.1 |

FOREIGN PATENT DOCUMENTS

DE     19627311     1/1998

\* cited by examiner

*Primary Examiner* — Heidi M Eide
(74) *Attorney, Agent, or Firm* — Fitzpatrick, Cella, Harper & Scinto

(57) ABSTRACT

A dental orthodontic apparatus includes a carrier and fastening elements having rear holding and front parts. The carrier includes an elongated carrier piece having two sections and a carrier holding part. The fastening elements are arranged along the sections such that the front part of each element is adjacent a front side of a section, and the rear holding part of each fastening means is adjacent a rear side of the section. Carrier piece material at the rear side of a section is removable by a fabrication tool. The rear holding part of each fastening element is embedded within and completely surrounded by a first section of the carrier piece, and the rear holding part of each fastening element is embedded within and completely surrounded by a second section of the carrier piece.

20 Claims, 3 Drawing Sheets

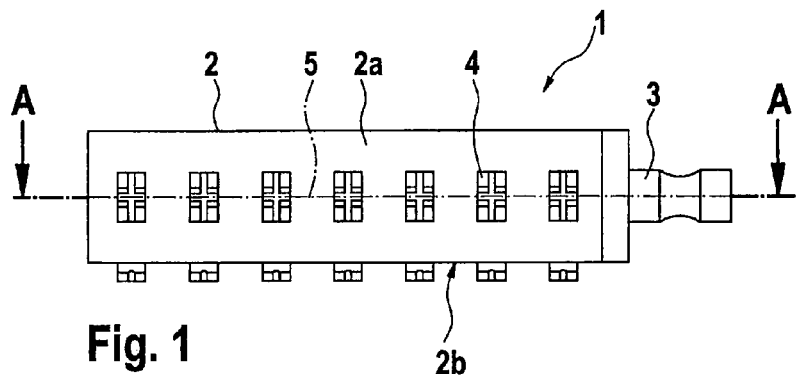
Fig. 1
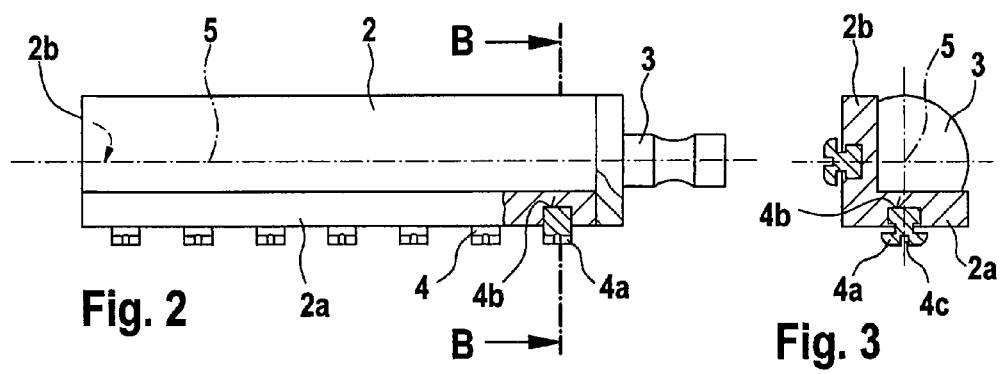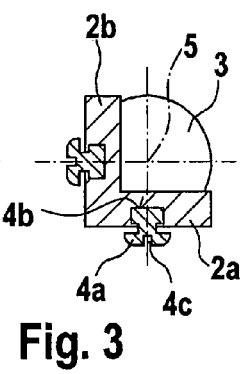
Fig. 2    Fig. 3
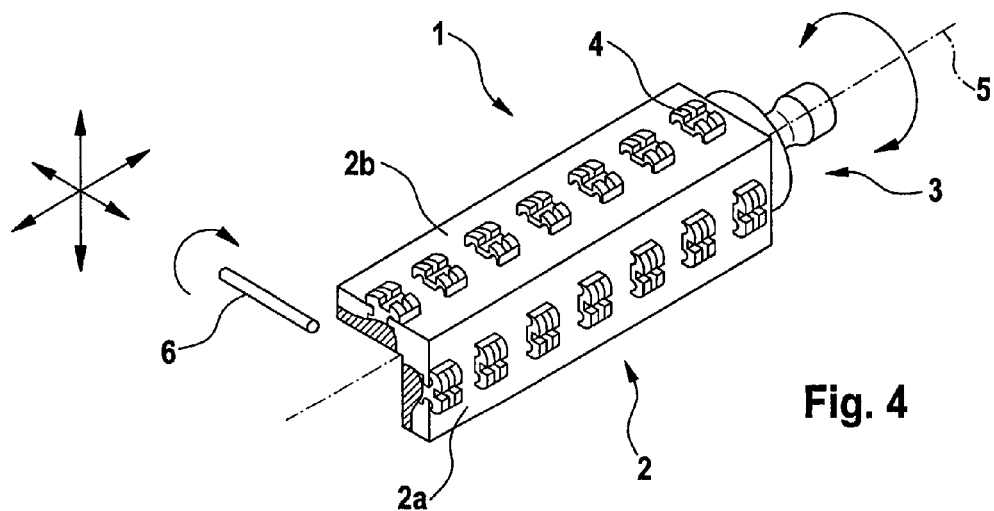
Fig. 4

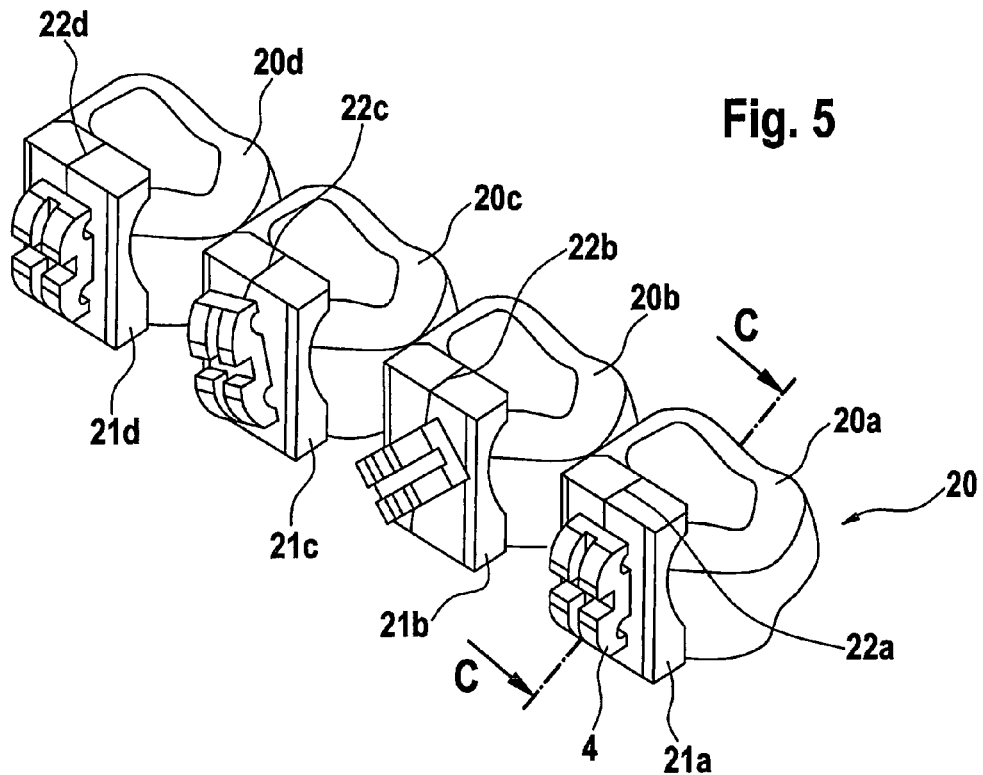
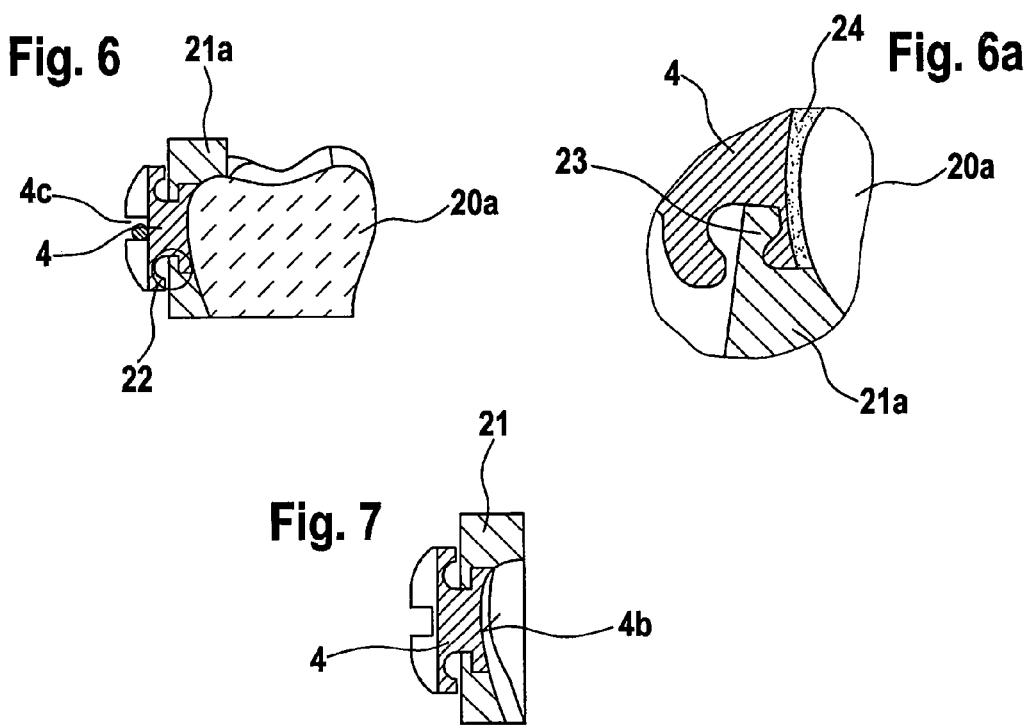

CARRIER FOR A FASTENING ELEMENT TO BE FABRICATED AND A METHOD FOR PRODUCTION THEREOF, PARTICULARLY AS AN ORTHODONTIC BRACKET

CROSS-REFERENCE RELATED APPLICATION

This application is related to U.S. Provisional Application No. 60/755,085, filed Jan. 3, 2006, the priority of which is hereby claimed, and it claims priority of German Patent Application No. 10 2005 025 5574, filed Jun. 1, 2005.

FIELD OF THE INVENTION

The invention relates to a carrier for a fastening element to be fabricated, a fastening element and a method for the production of this fastening element, particularly as an orthodontic bracket.

THE PRIOR ART

DE 693 27 661 T2 discloses the production of an orthodontic bracket whereby a slot for an arch wire is cut into a bracket blank. Cutting of the slot is performed according to individual requirements after a corresponding computation by means of a program. A holding piece constructed individually for each tooth is fabricated for the individually constructed bracket made from round plastic disks. The radius of the cutter of the fabricating tool is thereby taken into consideration.

It is of disadvantage in this case that the individual conditions of the attachment area on the tooth are not taken into consideration even with the individual design of the slot and the holding piece. This has the result that adjustment to the individual conditions is achieved totally through the amount of adhesive material or cement and this material has to transfer holding forces through different thicknesses.

Attention has to be paid additionally that the specific assignment of individual holding pieces and of individual brackets does not get lost, thus requiring great care during transport or during the subsequent installation.

U.S. Pat. No. 4,284,405 discloses a device and a method for orthodontic care wherein a model of the tooth situation is created and whereby a plate-like fixture is formed for positioning of the orthodontic appliance.

US 2004/0219473 discloses an orthodontic device which is positioned on the tooth with the aid of a replica of the tooth surface. The replica is produced with the aid of a teeth impression.

US 2003/0194677 A1 discloses a method and a device for the production of an orthodontic template assisting in the positioning of an orthodontic device. The template is designed with the aid of a computer based on the data set of the patient's tooth situation and it is manufactured by means of grinding, three-dimensional pressing and/or molding from a molten mass.

The disadvantage of the aforementioned orthodontic methods and devices is the fact that the orthodontic fastening devices have a standard geometry which cannot be adjusted to the geometry of the tooth surface. In addition, a great number of working steps are necessary for the realization of the methods mentioned above.

Based on the known methods and devices there is created the desire for a simple, cost-effective and realizable solution to produce orthodontic devices which can be accurately positioned and which can be manufactured based on a CAD/CAM processing plan with traditional commercial and proven automatic grinding/finishing machines.

SUMMARY OF THE INVENTION

The carrier according to the invention is provided with a holding piece for fastening in the receiving part of a finishing machine whereby the carrier comprises a carrier piece for the fastening element. The fastening element or bracket is at least partially embedded in the carrier piece in a manner so that the attachment area of the fastening element can be fabricated. A carrier can be clamped into a finishing machine and shaped therein and the attachment area of the fastening element can be individualized thereby.

The fastening element is advantageously a bracket used in the field of dental orthopedics with a pre-manufactured holding part at the front or with a holding part to be formed for an additional attachable component and an attachment area at its rear side for fastening to a tooth.

The fastening element is advantageously connected to the carrier piece at a lateral region between its front and rear side. This makes possible easy accessibility of the tools of the finishing machine to the fastening element.

The connection is advantageously designed as a connection with positive fit whereby especially a snap connection is preferred. Such a snap connection of a suitable design can be disconnected easily.

At least two fastening elements are provided on the carrier at a distance apart. The number of fastening elements to be finished by the respective finishing machines is usually considerably greater compared to finishing large-sized fastening elements so that the efficient production of several brackets is made possible in one working step, especially if the fastening elements are orthodontic brackets. As a rule, a large number of brackets are required at the same time in orthodontic care. The attachment of several fastening devices on one carrier is therefore highly economical.

The fastening elements are advantageously arranged along a longitudinal axis of the carrier piece. This makes fabrication in the finishing machine easier.

The carrier piece is advantageously provided with two sections arranged about the longitudinal axis. It is made possible thereby to double the number of fastening devices to be fabricated in one working step by having nearly the same space requirements as a one-sided carrier piece.

At least two sections are preferably connected to one another by the same material and they are preferably aligned to one another at an angle of 75 degrees to 90 degrees. Both sections are then highly accessible for the finishing machine.

It is especially advantageous if the fastening elements are arranged on the sections along the longitudinal axis in an offset manner. This makes a quicker finishing process possible.

The attachment area of the fastening element is advantageously totally embedded into the carrier piece. A carrier of this type can be produced in an especially cost-effective way.

The fastening element advantageously projects past the carrier piece with a holding piece for a tensioning element. This makes easier subsequent gripping and positioning of the holding piece on the tooth surface.

The material of the fastening element and the material of the carrier part is different so that an adhesive used for attachment of the fastening element to the tooth adheres only to the fastening element itself. The carrier piece is thereby prevented from being also glued to the tooth whereby especially easy manipulation of the carrier piece is achieved relative to the fastening element.

The fastening element is made of metal and the carrier piece is made of a polymeric material in an especially advantageous embodiment. A metal fastening element has sufficient stability for employment in orthodontic care and it is bio-compatible with the appropriate choice of material.

As an alternative it is possible to make the fastening element of a ceramic. Ceramic has especially good aesthetic characteristics since it is possible to adjust the color of the ceramic to the color of the tooth.

The carrier piece advantageously made of PTFE (polytetrafluoroethylene). PTFE, which is often called Teflon, can be processed well in finishing machines and does not adhere to many adhesives.

The holding part of the fastening element can also advantageously be shaped in a manner to influence the direction of action for the additional component to be attached. This makes possible the employment of straight, non-deformed wires (straight wire technology) whereby the bending of wires for the defined creation of forces upon individual teeth is no longer necessary or it is greatly simplified.

A predetermined breaking point is advantageously provided in the carrier piece adjacent to the attachment area of the fastening element. This makes the removal of the carrier piece easier during attachment of the fastening element to the tooth.

The carrier piece is advantageously manufactured using injection molding technology and the fastening element is embedded into the carrier piece as an inserted part (i.e., completely in contact with the carrier piece). Such a carrier piece can be manufactured in a highly cost-effective manner.

It is especially of advantage if at least fourteen fastening elements are provided on the carrier whereby the fastening elements are preferably designed differently from one another. At least fourteen fastening elements are usually required for each jaw in orthodontic care. Specific requirements are placed on the fastening elements depending on the location of employment which are reflected in the different design of the fastening elements.

An additional object of the invention relates to a fastening element having an attachment area whereby this attachment area is surrounded with an auxiliary positioning part. The attachment area and the auxiliary positioning part are individually shaped in a finished condition and they have, at least sectional, the shape of the surface onto which the fastening element is to be attached. Such an individually fabricated fastening element can be shaped in a manner so that it is possible to attach the fastening element onto the tooth with its attachment area by means of a uniformly thick adhesive layer, on the one hand, and to be able to vary the spatial orientation of the fastening element in many parameters, on the other hand (orientation of the front holding device, distance of the front holding device between the tooth, etc.)

The attachment area is advantageously covered by the auxiliary positioning part in an unfinished condition. It is made possible thereby to shape the auxiliary positioning part according to the natural arch of the tooth.

The attachment area of the fastening element is not covered by the auxiliary positioning part in the finished condition. This makes attachment of the fastening element to the tooth surface possible.

The auxiliary positioning part is advantageously provided with a predetermined breaking point. The auxiliary positioning part can thereby be easily removed from the tooth after positioning of the fastening element.

It is alternatively possible to attach the auxiliary positioning part to the fastening element by means of a detachable connecting piece. Advantageously, the detachable connection can be a snap connection.

It is of special advantage if the attachment area is set back relative to the auxiliary positioning part by an offset from the surface onto which the fastening element is to be attached. This allows enough space for application of a suitable adhesive whereby the set-back is chosen to correspond to the desired thickness of the adhesive.

In a method to produce a fastening element to be finished and to be attached to an individual surface, particularly in the field of dental orthopedics as an orthodontic bracket, the contour of the attachment area is defined with the aid of data of the surface onto which the fastening element is to be attached whereby a pre-shaped, not yet individualized fastening element is formed by removal of material to produce the specific contour. In addition, an auxiliary positioning part is provided with a contour that is continued by the contour of the attachment area and which is also defined by the surface onto which the fastening element is to be attached.

This fabrication can be achieved especially in a grinding machine suitable for finishing dental ceramic.

The fasting element is advantageously provided with a not yet individualized holding piece for a component to be held in place, whereby the holding piece is disposed on the side facing away from the attachment area and whereby the holding piece is shaped to conform to the individual surface of the component to be held with consideration of the orientation of the component. It is made possible thereby to design the fastening element in a manner so that a straight wire can be used. The determination of the amount of forces to be applied to the individual tooth is achieved through the position and orientation of the fastening element and of the holding piece on the tooth.

The attachment area of the fastening element is set back relative to the contour of the auxiliary positioning part by an offset from the surface onto which the fastening element is to be attached. A gap for the adhesive is created thereby which can be filled with a thick adhesive layer, depending on the distance of the offset, whereby the fastening element can be positioned and attached to the tooth with a very high accuracy in positioning and by having an adhesive layer of defined thickness.

The invention will now be better understood by reference to the attached drawings.

BRIEF DESCRIPTION OF THE DRAWINGS

FIG. 1 shows a carrier with a plurality of fastening elements in the form of brackets;

FIG. 2 shows a partial sectional view along line 2-2 of FIG. 1;

FIG. 3 shows a sectional view along line 3-3 of FIG. 2;

FIG. 4 shows a perspective view of the carrier together with a fabrication tool;

FIG. 5 shows a row of teeth with several glued-on brackets together with auxiliary positioning parts;

FIG. 6 shows a cross-sectional view along line 6-6 of FIG. 5 of a bracket with an auxiliary positioning part on a tooth;

FIG. 6a shows in detail a snap connection of the auxiliary positioning part on the bracket;

FIG. 7 shows the bracket together with the auxiliary positioning part from FIG. 6 without the tooth;

DETAILED DESCRIPTION OF THE PREFERRED EMBODIMENTS

Figure 8:
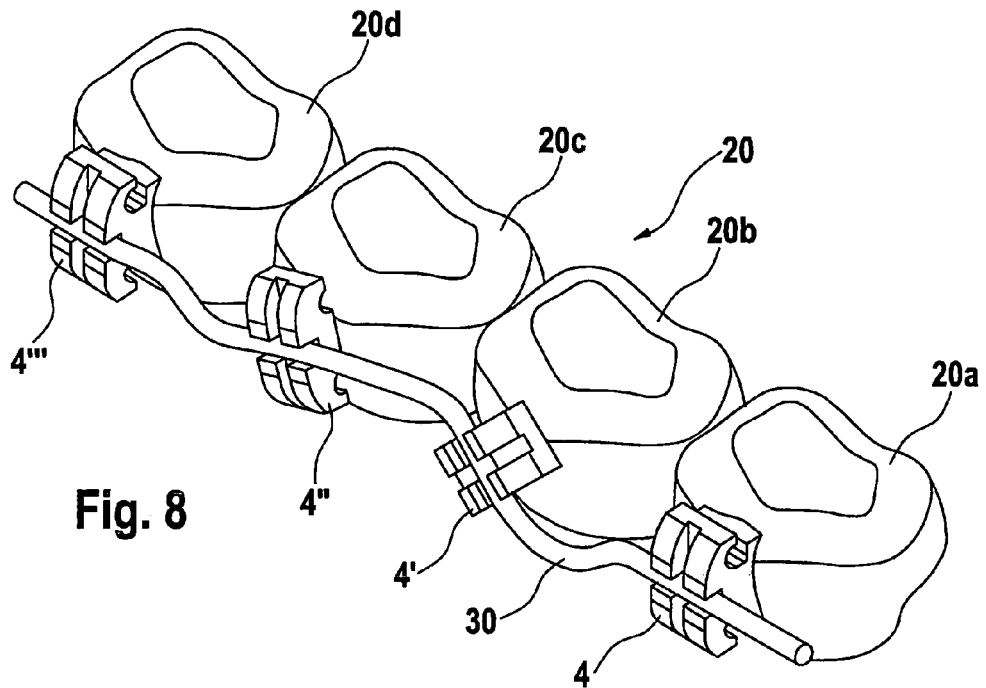
FIG. 8 shows the row of teeth from FIG. 5 after removal of the auxiliary positioning part and after the attachment of a tensioning wire.

FIG. 1 illustrates a carrier 1 comprising an elongated carrier piece 2 and a holding part 3 attached to a longitudinal end of the carrier piece for attachment to a (non-illustrated) receiving part of a finishing machine. A plurality of fastening elements 4 are arranged in the carrier piece 2. The fastening elements 4 are juxtaposed along a longitudinal axis 5 of the carrier.

FIG. 2 shows a sectional view along line 2-2 in FIG. 1. Portions of the fastening elements 4 project outwardly of the carrier piece 2. It can be clearly seen in conjunction with FIG. 3 that the carrier piece 2 consists of two sections 2a and 2b which are one piece and which form an angle of approximately 90 degrees. Section 2a and section 2b are accessible from the rear, which means the side facing the longitudinal axis 5, for finishing with a fabrication tool.

It can be seen furthermore that one side of each fastening element 4 facing away from the carrier piece 2 is provided with a holding piece (front part) 4a which projects outwardly of the carrier piece, and an attachment area 4b which is completely embedded in, and surrounded by the material of, the carrier piece 2 which is formed of a block of material.

The holding piece 4a of the fastening element 4 is already provided with a slot 4c to receive a tensioning element (not illustrated). The slot 4c is either contained in the still unfinished carrier 1 or it is individually fabricated in a finishing process of the carrier 1 by means of a suitable fabrication tool with a fixed setting corresponding to the fastening elements.

FIG. 4 shows in a perspective view the carrier 1 from FIG. 1 through FIG. 3. In addition, there is shown the pin-shaped fabrication tool 6 in the form of a grinder or cutter which can be moved in a relative movement corresponding to the spatial axes of the carrier 1 as illustrated by arrows. The inner side of the section 2a can be worked on in the shown position of the carrier 1 to produce a predetermined contour. The carrier piece 2 is finished in the region of the attachment area 4b during the material-removing process to such a degree that the attachment area is completely laid open and is no longer covered by the material of the carrier piece 2. The area of the carrier piece 2 adjacent to the attachment area 4b is also finished whereby the contour of the attachment area is continued.

Nevertheless, it is possible to produce a separate auxiliary positioning part based on the existing surface data and to attach this auxiliary positioning part at a later time on the fastening element preventing simultaneous production, on the one hand, and faulty arrangement of the positioning part to fastening part, on the other hand.

FIG. 5 shows a row of teeth 20 made up of the teeth 20a through 20d whereby the bracket 4 is attached to the teeth together with the surrounding part of the former carrier piece 2 designed as an auxiliary positioning part 21. It can be seen that the auxiliary positioning part on tooth 20a is oriented approximately axis-parallel to the fastening element 4, whereas the auxiliary positioning part 21b on tooth 20b is rotated clockwise relative to the fastening element 4. An auxiliary positioning part 21c on tooth 20c is rotated in an opposite direction compared to the one on tooth 20b and the auxiliary positioning part 21d on tooth 20d is again oriented approximately axis-parallel.

Even though the fastening elements in the carrier are all oriented the same according to FIG. 1, an auxiliary positioning part can be provided through specific fabrication leading to a slanted position of the fastening element relative to the other fastening element. It is required thereby that the number of fastening elements in FIG. 1 have sufficiently large spaces between each other on the carrier piece 2.

FIG. 6 shows a sectional view along line 6-6 in FIG. 5. A fastening element 4 is attached to tooth 20a either with adhesive or cement. The orientation of the fastening element 4 on tooth 20a is achieved by means of the auxiliary positioning part 21a which is connected in turn to the fastening element 4 with a snap connection 23. Care has to be taken during attachment of the fastening element 4 to tooth 20a so that the auxiliary positioning part 21a itself is not bonded to tooth 20a. The adhesives or the types of cement used to attach the fastening element 4 will not bond with the auxiliary positioning part itself if the auxiliary positioning part is made of a material such as PTFE, for example.

The snap connection 23 is illustrated in FIG. 6a and it can be seen that the auxiliary positioning part 21a is provided with a snap-on projection engaging the cutout on the fastening element 4. In addition, this cutout is additionally helpful during removal of the bonded fastening element 4 from tooth 20a.

The auxiliary positioning parts 21a through 21d are provided with predetermined breaking points 22a through 22d for easier removal of the positioning parts after attachment 4a through 4d to the teeth 20a through 20d.

Even though there is not shown in FIG. 6 a receiving slot 4c with an axis-parallel orientation, the slot can still extend in another direction as it is already known and required in the production of brackets to pull the tooth 20a downward or to lift it up, for instance.

FIG. 7 reflects the position of the attachment area 4b of the fastening element 4 whereby the contour of the attachment area 4b conforms to the predetermined surface of tooth 20a, possibly with consideration of a correction value for the bonding material, particularly adhesive or cement. The positioning area of the auxiliary positioning part 21 laterally abuts the attachment area 4b whereby the contour of the auxiliary positioning part conforms to the surface of tooth 20. A gap measurement is not required to be taken into consideration here since no bonding material is used such as an adhesive or cement.

The position of an adhesive layer 24 is shown in FIG. 6a. It can be additionally advantageous to provide compensation spaces in the auxiliary positioning part 21a to receive excess bonding material such as adhesive or cement (not illustrated).

FIG. 8 illustrates the row of teeth 20 from FIG. 5 after a tensioning element 30 has been inserted into the fastening elements 4 and after the auxiliary positioning part 21 has been removed.

The tensioning element 30 is a straight wire with defined elasticity, which is tensioned in a bent shape through the position and orientation of the fastening elements 4, 4', 4", 4'" on the teeth 20a through 20d and the position of the holding pieces 4c. The tensioning element 30 exerts a defined translatory and/or rotatory force on each of the teeth 20a through 20d through its elasticity corresponding to its curvature whereby the force leads to the desired displacement of the respective teeth 20a through 20d.

Removal of the auxiliary positioning part is easily possible after bonding of the fastening element 4 since is consists of a non-adhesive material, e.g., Teflon, and it can be simply taken off by means of the snap connected and/or the predetermined breaking point. Only the accurately positioned fastening element 4 remains now on the tooth.

The positioning of the fastening element 4 on the tooth 20a with its connected auxiliary part 21 is achieved in that a position is searched by moving the fastening element along tooth 20 whereby the largest coverage of the outer surface of tooth 20 is made with the inner surface of the fastening element 4 or of the auxiliary positioning part 21. A firm connection is created through pressing of the fastening element 4 against the tooth 20, possibly under the simultaneous influence of heat and/or light.

Displacement by sliding of the fastening element and its connected auxiliary positioning part 21 is prevented in that a much greater contact surface exists between tooth 20 and the auxiliary positioning part 21 after reaching the fitting position than before so that a considerably greater force would be necessary to push the auxiliary positioning part 21.

The fastening element 4 can be moved to a small degree relative to the surrounding auxiliary positioning part 21 in that the attachment area 4b of the fastening element 4 is set back relative to the positioning area of the auxiliary positioning part 21 whereby the snap connection allows a certain tolerance of movement toward the attachment area 4b. The fastening element 4 is thereby guided along the sides of the surrounding positioning part 21.

It is achieved thereby that a small gap is developed between the fastening element 4 and the extension of the surface of the auxiliary positioning part 21 whereby the gap is filled with an adhesive and a uniformly thick adhesive layer is created thereby.

Forces developed during fabrication are easily absorbed during manufacturing of the recess 4c in that the fastening element 4 is completely embedded in the carrier piece at the side of the attachment area 4b. Shaping of the attachment area 4b and fabrication of the auxiliary positioning part, which is formed from the carrier piece 2, occurs only after the fabrication of the recess 4c.

Figure 9:
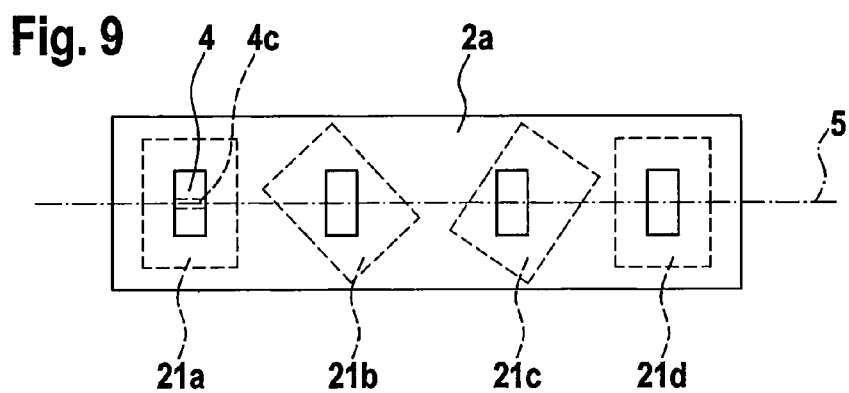
FIG. 9 shows the arrangement of the brackets and the auxiliary positioning parts from FIG. 1.

FIG. 9 illustrates how the auxiliary positioning parts 21a through 21d from FIG. 5 can be produced from the carrier part shown in FIG. 1.

Figure 10A:
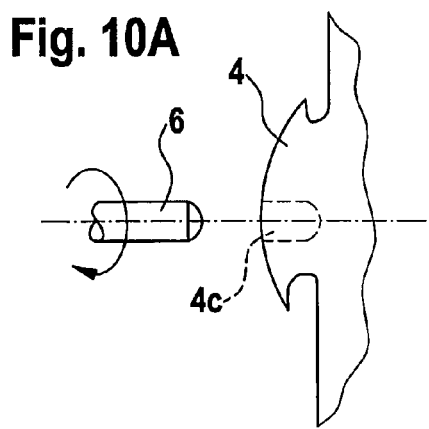
FIG. 10A shows the fabrication of a bracket to produce a first design of a receiving part for a tensioning element.
Figure 10B:
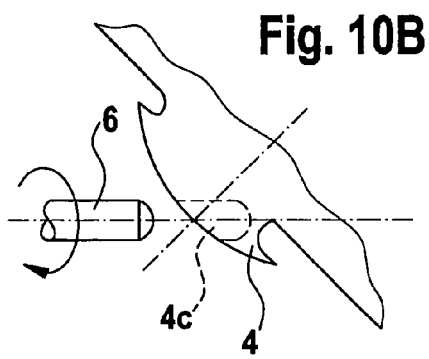
FIG. 10B shows the fabrication of the bracket to produce a second design of a receiving part for a tensioning element.

FIG. 10 illustrates how a recess 4c is produced in the fastening element 4 extending straight across or at an angle. This can be achieved through rotating of the carrier 1 about its longitudinal axis 5 corresponding to FIG. 4 and this longitudinal axis must be in place should there be proposed more than one carrier section provided with fastening elements so that the fabrication tool 6 can reach the attachment areas of the fastening elements.

As an alternative to the placement of the fastening element 4 relative to the auxiliary positioning part 21 illustrated in FIG. 9, which is essentially defined by the direction of the recess 4c, it is also conceivable to place the auxiliary positioning part 21 and the fastening element 4 always parallel to one another and to give the recess also the desired direction along the directional axis 5 through corresponding fabrication.

I claim:

1. A combination of first fastening elements and second fastening elements for use as a bracket in dental orthodontics, each of said fastening elements having a rear holding part and a front part, and a carrier for said fastening elements, said carrier including an elongated carrier piece having a longitudinal axis and formed of a block of material having two sections, and a carrier holding part for mounting the carrier piece to a finishing machine having a fabrication tool, the carrier holding part being connected to a longitudinal end of the carrier piece,
wherein:
the first fastening elements are arranged along a first one of the two sections of the block of material such that the front part of each first fastening element is adjacent a front side of the first section, and the rear holding part of each first fastening element is adjacent a rear side of the first section,
the second fastening elements are arranged along a second one of the two sections of the block of material such that the front part of each second fastening element is adjacent a front side of the second section, and the rear holding part of each second fastening element is adjacent a rear side of the second section,
the material of the carrier piece at the rear side of each of the two sections is removable by the fabrication tool,
the rear holding part of each first fastening element is embedded within and completely surrounded by the first section of the carrier piece, and
the rear holding part of each second fastening element is embedded within and completely surrounded by the second section of the carrier piece.

2. The combination according to claim 1, wherein the sections are one piece and form an angle therebetween of about 75 degrees to about 90 degrees.

3. The combination according to claim 1, wherein the fastening elements are arranged offset to one another on the sections along a longitudinal axis.

4. The combination according to claim 1, wherein the material of the fastening elements and the material of the carrier piece are different, and including an adhesive used for attachment of a fastening element to a tooth which adheres only to the fastening element itself.

5. The combination according to claim 4, wherein the fastening elements comprise metal and wherein the carrier piece comprises a polymeric material.

6. The combination according to claim 4, wherein the fastening elements comprise ceramic and wherein the carrier piece comprises a polymeric material.

7. The combination according to claim 4, wherein the carrier piece comprises PTFE (polytetrafluoroethylene).

8. The combination according to claim 1, wherein the carrier holding part and the fastening elements are shaped to influence the direction of action of an additional component to be attached.

9. The combination according to claim 1, wherein the carrier piece defines a predetermined breaking point adjacent to an attachment area of a fastening element.

10. The combination according to claim 1, wherein the carrier piece is injection molded and the fastening elements are embedded in the carrier piece as inserted parts.

11. The combination according to claim 1, comprising fourteen fastening elements, each fastening element being shaped differently.

12. A dental orthodontic apparatus comprising:
first fastening elements and second fastening elements for orthodontic use, each of the fastening elements having a rear holding part and a front part; and
a carrier including an elongated carrier piece having a longitudinal axis and formed of a block of material having two sections and a carrier holding part to mount the carrier piece to a finishing machine having a fabrication tool, the carrier holding part being connected to a longitudinal end of the carrier piece, wherein:
the first fastening elements are arranged along a first one of the two sections of the block of material such that the front part of each first fastening element is adjacent a front side of the first section, and the rear holding part of each first fastening element is adjacent a rear side of the first section,
the second fastening elements are arranged along a second one of the two sections of the block of material such that the front part of each second fastening element is adjacent a front side of the second section, and the rear holding part of each second fastening element is adjacent a rear side of the second section,
the material of the carrier piece at the rear side of each of the two sections is removable by the fabrication tool,
the rear holding part of each first fastening element is embedded within and completely surrounded by the first section of the carrier piece, and
the rear holding part of each second fastening element is embedded within and completely surrounded by the second section of the carrier piece.

13. A dental orthodontic apparatus according to claim 12, wherein the two sections form a substantially right angle therebetween.

14. A dental orthodontic apparatus according to claim 12, wherein the material of the carrier piece and the material of the fastening elements are different.

15. A dental orthodontic apparatus according to claim 14, wherein the fastening elements comprise one of metal and ceramic.

16. A dental orthodontic apparatus according to claim 14, wherein the carrier piece comprises one of a polymeric material and PTFE (polytetrafluoroethylene).

17. A dental orthodontic apparatus according to claim 12, further comprising an adhesive for attaching the fastening elements to teeth.

18. A dental orthodontic apparatus comprising:
first fastening means and second fastening means for fastening, each fastening means having a rear holding part and a front part and being for orthodontic use; and
carrier means including an elongated carrier piece having a longitudinal axis and formed of a block of material having two sections and carrier holding means for mounting the carrier piece to a finishing machine having a fabrication tool, the carrier holding means being connected to a longitudinal end of the carrier piece,
wherein:
the first fastening means are arranged along a first one of the two sections of the block of material such that the front part of each first fastening means is adjacent a front side of the first section, and the rear holding part of each first fastening means is adjacent a rear side of the first section,
the second fastening means are arranged along a second one of the two sections of the block of material such that the front part of each second fastening means is adjacent a front side of the second section, and the rear holding part of each second fastening means is adjacent a rear side of the second section,
the material of the carrier piece at the rear side of each of the two sections is removable by the fabrication tool,
the rear holding part of each first fastening means is embedded within and completely surrounded by the first section of the carrier piece, and
the rear holding part of each second fastening means is embedded within and completely surrounded by the second section of the carrier piece.

19. A dental orthodontic apparatus according to claim 18, wherein the two sections form a substantially right angle therebetween.

20. A dental orthodontic apparatus according to claim 18, further comprising means for attaching the fastening means to teeth.

\* \* \* \* \*

UNITED STATES PATENT AND TRADEMARK OFFICE
CERTIFICATE OF CORRECTION

| | | |
|---|---|---|
| PATENT NO. | : 8,636,505 B2 | Page 1 of 1 |
| APPLICATION NO. | : 11/436051 | |
| DATED | : January 28, 2014 | |
| INVENTOR(S) | : Peter Fornoff | |

It is certified that error appears in the above-identified patent and that said Letters Patent is hereby corrected as shown below:

ON TITLE PAGE AT ITEM (75) INVENTOR:

"Peter Fornoff, Relchelsheim (DE)" should read --Peter Fornoff, Reichelsheim (DE)--.

Signed and Sealed this
Twenty-first Day of October, 2014

Michelle K. Lee
*Deputy Director of the United States Patent and Trademark Office*